(12) United States Patent
Pitcher

(10) Patent No.: US 10,034,987 B2
(45) Date of Patent: Jul. 31, 2018

(54) ESSENTIAL OILS DIFFUSER

(71) Applicant: SPDI HOLDINGS, INC., Alpine, UT (US)

(72) Inventor: Stephen N. Pitcher, Alpine, UT (US)

(73) Assignee: SPDI Holdings, Inc., Alpine, UT (US)

( * ) Notice: Subject to any disclaimer, the term of this patent is extended or adjusted under 35 U.S.C. 154(b) by 0 days.

(21) Appl. No.: 15/287,733

(22) Filed: Oct. 6, 2016

(65) Prior Publication Data
US 2018/0099105 A1 Apr. 12, 2018

(51) Int. Cl.
*B01F 3/04* (2006.01)
*A61M 11/02* (2006.01)
*A61L 9/14* (2006.01)

(52) U.S. Cl.
CPC .............. *A61M 11/02* (2013.01); *A61L 9/145* (2013.01); *B01F 3/04106* (2013.01); *B01F 3/04241* (2013.01); *A61L 2209/132* (2013.01); *B01F 2215/009* (2013.01)

(58) Field of Classification Search
CPC .... B01F 3/04; B01F 3/04099; B01F 3/04106; B01F 3/04241
USPC ........... 261/26, 30, 121.1, DIG. 88; 422/124
See application file for complete search history.

(56) References Cited

U.S. PATENT DOCUMENTS

| | | | |
|---|---|---|---|
| 2,405,494 A | * | 8/1946 | Dupuy ................ F24F 6/12 261/120 |
| 6,645,436 B2 | | 11/2003 | Davis |
| 7,407,118 B2 | | 8/2008 | Sevy |
| 2002/0043568 A1 | | 4/2002 | Hess |
| 2004/0238976 A1 | | 12/2004 | Johns |
| 2007/0138326 A1 | | 6/2007 | Hu |
| 2010/0084484 A1 | | 4/2010 | Sevy |
| 2017/0106333 A1 | | 4/2017 | Zhu |

FOREIGN PATENT DOCUMENTS

| | | |
|---|---|---|
| CN | 202566815 U | 12/2012 |
| CN | 204106638 U | 1/2015 |
| CN | 204972379 U | 1/2016 |
| CN | 205241636 U | 5/2016 |
| CN | 206139377 U | 5/2017 |
| CN | 206143854 U | 5/2017 |
| JP | 05-269189 A | 10/1993 |
| KR | 20-2014-0004200 U | 7/2014 |
| WO | 2011021980 A1 | 2/2011 |
| WO | 2015158970 A1 | 10/2015 |

OTHER PUBLICATIONS

Kim "International Search Report for Application No. PCT/US2017/055643" dated Jan. 11, 2018, 3 pages.
Kim "Written Opinion of the International Searching Authority for Application No. PCT/US2017/055643" dated Jan. 11, 2018, 3 pages.

* cited by examiner

*Primary Examiner* — Robert A Hopkins
(74) *Attorney, Agent, or Firm* — Perry S. Clegg; Kunzler, PC

(57) ABSTRACT

An essential oils diffuser with a micro air pump providing between 500 and 1500 Pa of pressure with a consumption of between 0.2 and 1 Watts may be used to push air into essential oils or an essential oil solution to diffuse and expel the oils into the air, while keeping the oils away from the air pump, preventing the oils from shortening the life of the diffuser. The diffuser may include a power supply and a controller to regulate the operation of the diffuser.

20 Claims, 5 Drawing Sheets

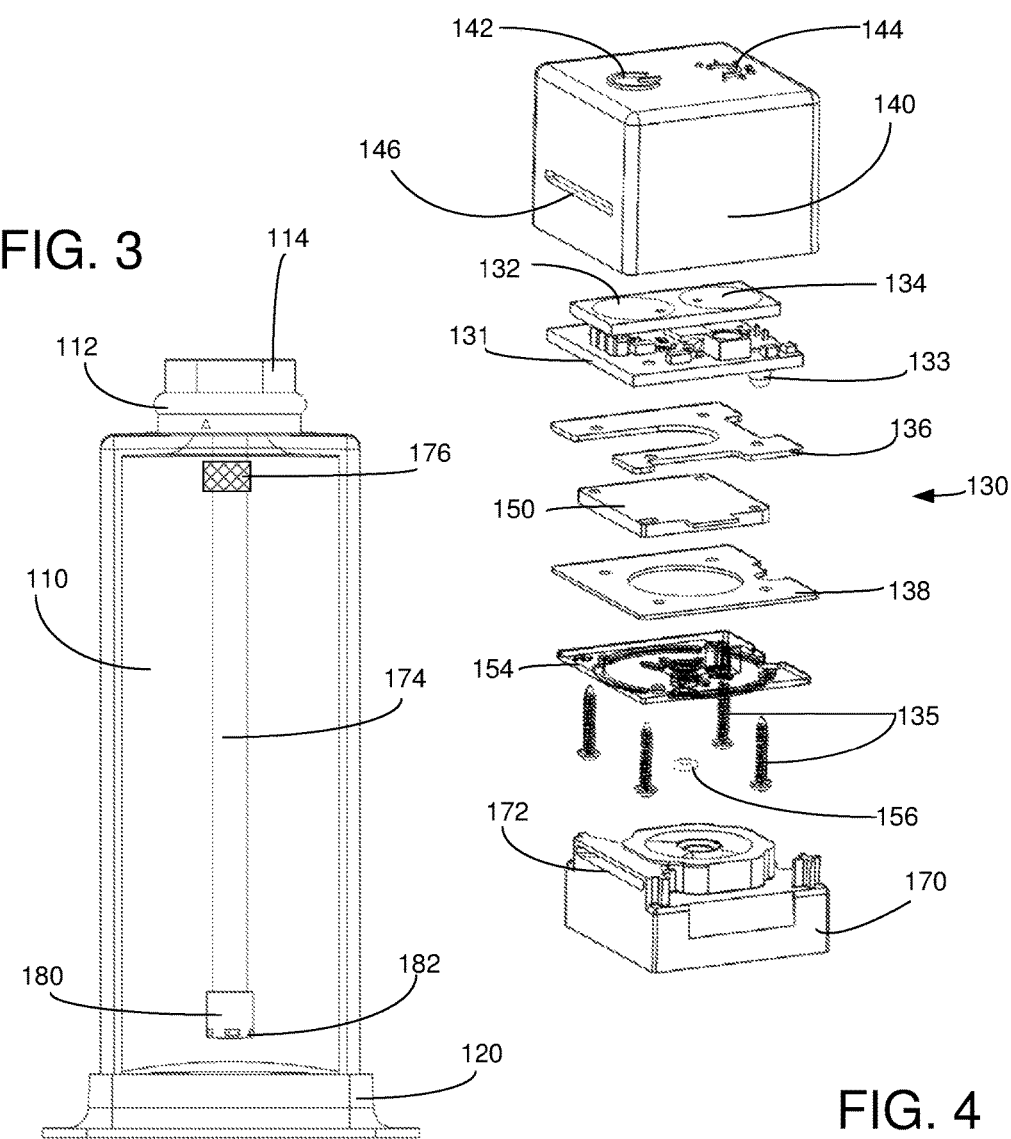

ESSENTIAL OILS DIFFUSER

PRIORITY

Not Applicable.

FIELD

This application relates generally to devices for dispersing essential oils into the air. In particular, this application relates to devices for dispersing essential oils into the air by infusing the oils with air and dispersing the saturated air.

BACKGROUND

In recent years, sales for essential oils have exploded. Essential oils are usually oils which are derived from, or include certain essential components or essences of different plant substances. Such oils are generally ingested, topically applied, or are breathed in through various methods of diffusion or atomization.

Essential oils, known as nature's living energy, are the natural, aromatic volatile liquids found in shrubs, flowers, trees, resins, fruit peels, rhizomes, roots, bushes, and seeds. The distinctive components in essential oils defend plants against insects, environmental conditions, and disease. They are also vital for a plant to grow, live, evolve, and adapt to its surroundings. Essential oils are extracted from aromatic plant sources via steam distillation, cold pressing, and other types of extraction and/or distillation. Essential oils are highly concentrated and far more potent than dry herbs. Other topically applied oils may include olive oil, almond oil, coconut oil, fatty acid oils, etc., and oils high in esters, such as jojoba oil, and waxes such as beeswax.

While essential oils often have a pleasant aroma, their chemical makeup is complex and their benefits vast—which makes them much more than something that simply smells good. Historically, essential oils have played a prominent role in everyday life. With more than 200 references to aromatics, incense, and ointments throughout the Bible, essential oils are said to be used for anointing and healing the sick. Today, essential oils are used for aromatherapy, massage therapy, emotional health, personal care, nutritional supplements, household solutions, and much more.

Diffusers for essential oils have been used to disperse the essential oils for breathing or to create a pleasant fragrance in a room or area. However, available diffusers for use with most essential oils are almost always unreliable with short service lives and high failure rate, and have to be refilled often. Additionally, most diffusers only operate for limited durations of a few hours before depleting the aromatic compounds. Many problems can be mitigated with meticulous care in maintaining the diffuser, which is beyond the capacity and patience of the average user.

Many types of available diffusers use a piezo-electric ultrasonic transducer to agitate the water's surface, where essential oils reside, into water and essential vapor. The water has essential oils mixed in, some of which is transported along with the water into the air with a blower or fan. One of the greatest complaints with these types of diffusers is the low intensity of the essential oil aromas produced. The piezo transducer is located within the water and oil reservoir. When the water runs out, or is left to sit and evaporate, residual oils tend to collect on the piezo transducer. Accumulations of the oils on the piezo transducer reduce the effectiveness, and eventually cause failure of the diffuser, often in very short order. Users are instructed to carefully clean the diffuser after each use, including cleaning the transducer with a detergent. However, users often neglect this task or clean too vigorously, damaging or destroying the sensitive piezo transducer.

Other diffusers use small fans or microblowers using traditional rotating fans. In small or micro fans, such microblowers are fairly inefficient, only supplying between about 5.5 and 60 Pa of pressure with a power consumption of between about 0.1 and 1.1 Watts with dimensions less than 25×25 mm. Any larger fans are not really microfans or microblowers. Such microfans also tend to have fairly short lives making diffusers run with such fans undesirable and inefficient. Additionally, such microfans are also unable to generate enough pressure through a small tube in order to push air through oil to create air saturated with oil for dispersion, but instead only generates sufficient air pressure to move air across the surface of oil, such as is shown in US Patent Pub. 2007/0138326.

SUMMARY

An essential oils diffuser with a micro air pump providing between 500 and 1500 Pa of pressure with a consumption of between 0.2 and 1 Watts may be used to push air into essential oils or an essential oil solution to infuse and expel the oils into the air, while keeping the oils away from the air pump, preventing the oils from shortening the life of the diffuser. The diffuser may include a power supply and a controller to regulate the operation of the diffuser.

BRIEF DESCRIPTION OF THE DRAWINGS

The following description can be better understood in light of Figures, in which:

FIG. 3 shows a bottle, straw, base, and bubbler of the essential oils diffuser of FIG. 1;

FIG. 4 shows and exploded view of a controller assembly and bottle interface, including as optional foaming reduction device for the essential oils diffuser of FIG. 1;

Figure 1:
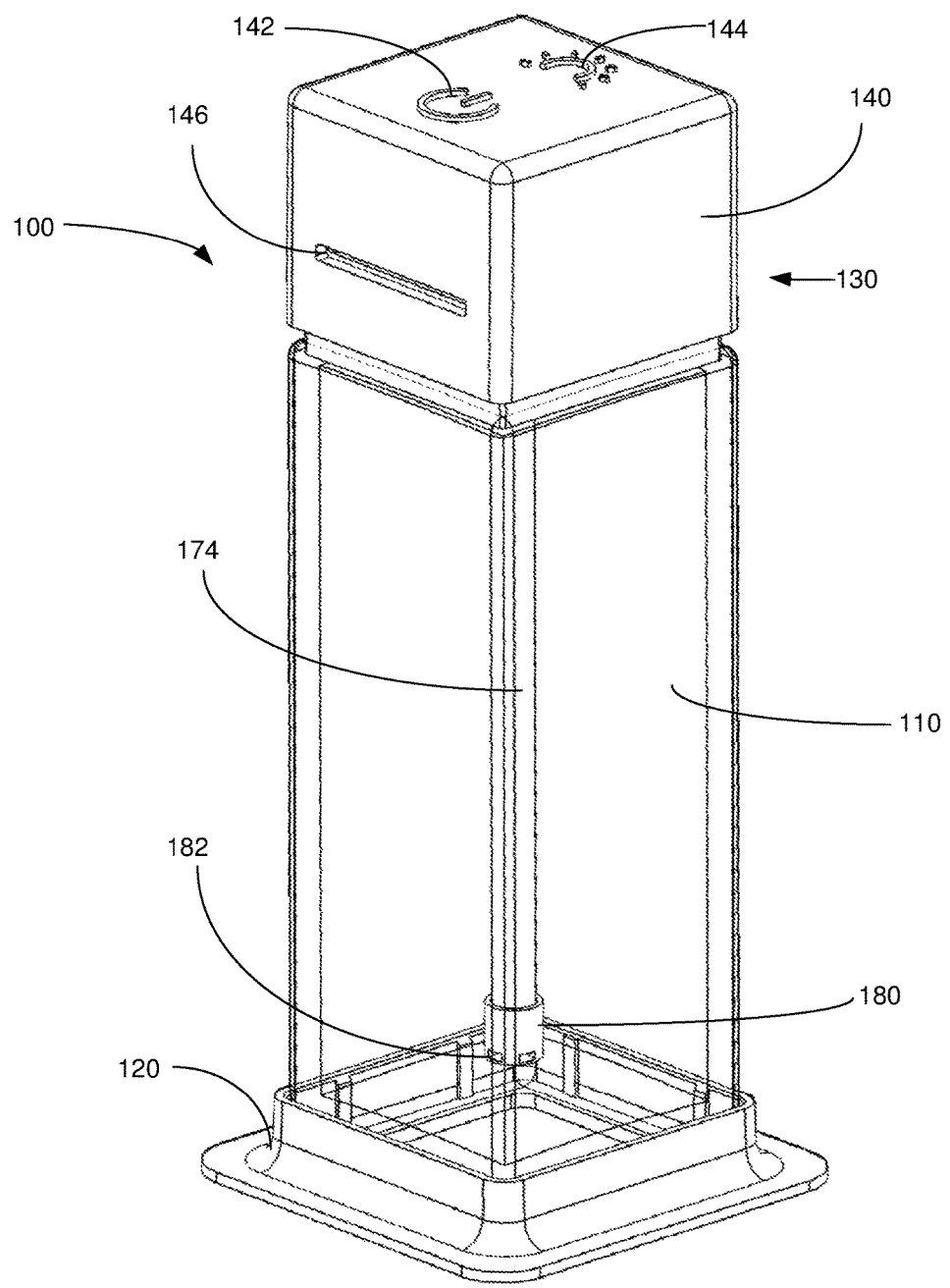
FIG. 1 shows an orthogonal view of an essential oils diffuser according to some embodiments.

Together with the following description, the Figures demonstrate and explain the principles of essential oil diffusers and methods for making and using such. In the Figures, the thickness and configuration of components may be exaggerated for clarity. The same reference numerals in different Figures represent the same component. Additionally, some components may be emphasized or not included in different drawings to illustrate particular features.

DETAILED DESCRIPTION

The following description supplies specific details in order to provide a thorough understanding. Nevertheless, the skilled artisan would understand that the apparatus and associated methods of using the apparatus can be implemented and used without employing these specific details. Indeed, the apparatus and associated methods can be placed into practice by modifying the illustrated apparatus and associated methods and can be used in conjunction with any other apparatus and techniques conventionally used in the industry.

Exemplary essential oils diffusers may utilize an optimized and unique design to effectively diffuse many different types of essential oils with or without any added water into a personal space or room for many hours and even days of enjoyment. Essential oils diffusers disclosed herein may use a piezoelectric micro air pump or other suitable micro air pump to create bubbles emitted from the bottom of within a well or reservoir of essential oils where the emitted bubbles rapidly percolate through the entire column of liquid. Creating bubbles in essential oils causes an efficient saturation of oil in the air within the air bubbles. Indeed, bubbles provide an efficient and dynamic oil infusion into the air by providing extended exposure of the air to a maximum surface area compared to volume of air, thereby infusing the bubble air with essential oils for dispersal in a room or other personal environment. Thousands of bubbles per minute may be created as they emit from the designed bubbler tip, located at the bottom of the tube. Furthermore, bubblers also provide a calming sound of bubbling water as compared to the high frequency whine of traditional air fans and blowers. Suitable micro air pumps may provide between 500 and 1500 Pa of pressure with a consumption of between 0.2 and 1 Watts and deliver about 1 L/min of airflow in a physical package of less than 25×25×10 mm.

Through experimentation, it was discovered that a head pressure of at least 500 Pa is required to create sufficient bubbles 1 inch (25.4 mm) under the surface of light viscosity essential oils. Heavier essential oils and deeper reservoirs, or course, require higher pressures to permit bubbling. It was also discovered that commercially available traditional fan and blower designs were incapable of delivering the required pressure for submerged bubbling air infusion to push air into essential oils or an essential oil solution to diffuse and expel the oils into the air, while keeping the oils away from the air pump, preventing the oils from shortening the life of the diffuser. As shown in the Figures, essential oils diffusers 100 that are suitable to generate effective, efficient submerged bubbling diffusion may include a controller assembly 130, a reservoir (bottle) 110, base 120, and a tube 174 and bubbler 180 that extend into the reservoir 110. Effective diffusers using the components illustrated may measure less than 155 mm tall including reservoir and less than 30×30 mm, with a controller/air pump assembly of less than 30 mm cubed to provide an efficient, effective micro diffuser.

Figure 2:
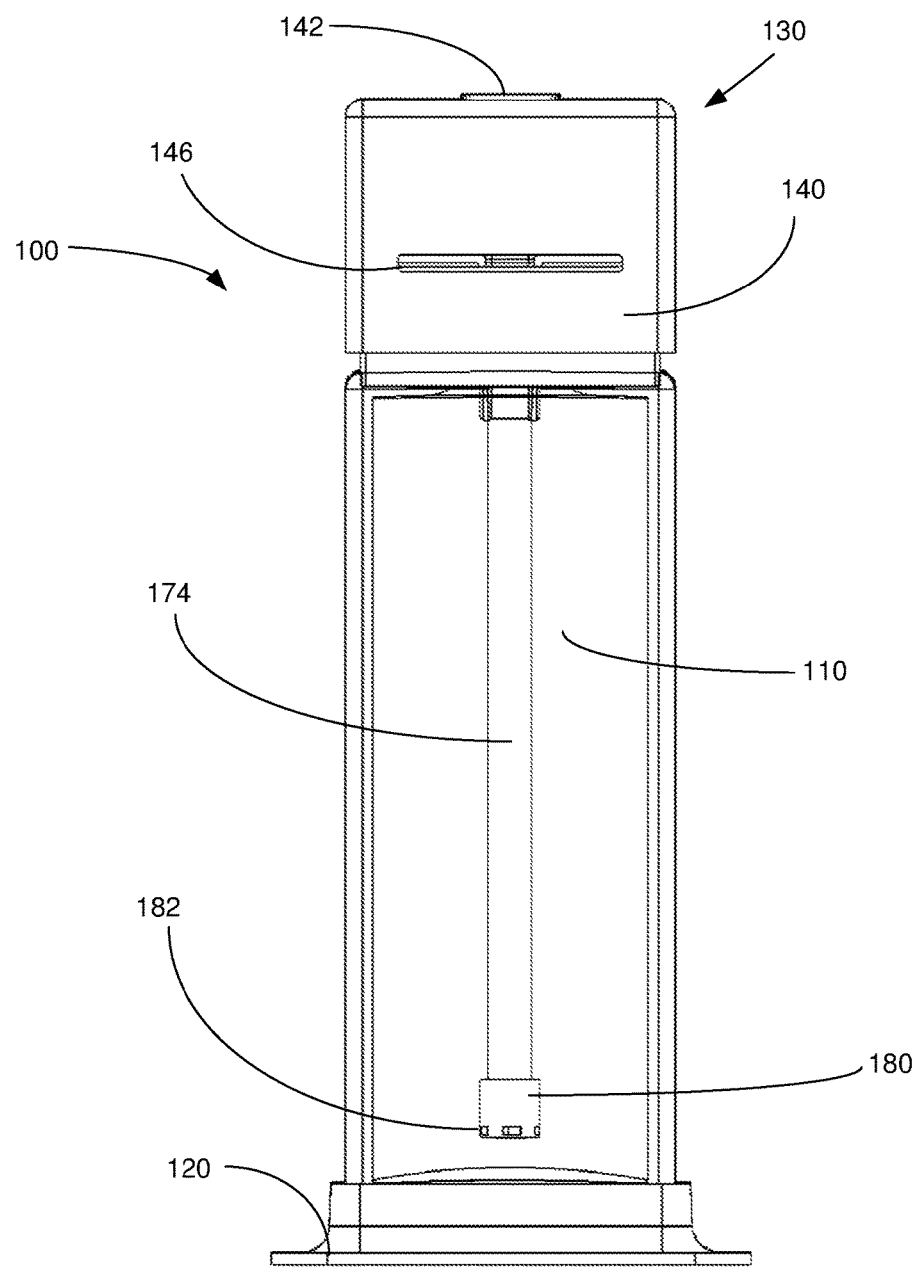
FIG. 2 shows a front view of the essential oils diffuser of FIG. 1.

Turning first to FIGS. 1 and 2, diffuser 100 may include a controller assembly 130 with a protective cap 140 mounted on a reservoir 110. Reservoir 110 may be placed in base 120 to stabilize diffuser 100 to reduce the likelihood of spills, tip overs, or unwanted vibrations. In addition, controller assembly 130 may be equipped with a tilt sensor to automatically shut down the diffuser in the event of a tipped condition. Protective cap 140 may house the controller assembly 130, which will be discussed in more detail below, oil infused air exhaust 146, and buttons 142 and 144 for operating diffuser 100. Controller assembly 130 may be removably secured to reservoir 110 using gaskets and may include tube 174 extending from the bottom of controller assembly 130 and to near the bottom of reservoir 110. At the end of tube 174, bubbler 180 may include a plurality of holes 182 to bubble air into essential oils within the reservoir. As shown in FIG. 3 a bubble disruptor 176 may be included on tube 174 to keep any oil bubbles from pushing liquid oil out through cap base 170 and exhaust opening 146 to prevent oil sputter or droplets from collecting around diffuser 100.

FIGS. 3 and 4 shown exploded views of the various components and will be used to explain the various components of the illustrated embodiments and the function of diffuser 100. Controller assembly 130 may include cap 140 covering the internal components and providing an aesthetic package for diffuser 100. Pressure pad electronic switches 132 and 134 may be operated by pushing buttons 142 and 144 of cap 140. Button 142 may be used to select air flow rates and button 144 may be used to select lighting of one or more LEDs 133 to provide an attractive aesthetic to diffuser 100. The internal components may include a printed circuit board controller 131 with electronic components to provide light and control micro air pump 150. Controller 131 may include wireless capabilities, and may be programmable using a USB or other suitable interface. Similarly, a USB cord may be used to power diffuser 100 because of the low power requirement of micro air pump 150 and controller assembly 130.

Micro air pump 150 may be a piezo air pump meeting the specifications discussed above. Spacers 136 and 138 may be provided to separate the fresh air supply into air pump 150 and the output air from air pump 150. Pump base 154 may be secured to controller 131 with fasteners 135 to secure the controller/air pump assembly 130 together. Gasket 156 may be used to create an air tight interface between the air output of air pump 150 and cap base 170.

Cap base 170 may be formed to secure controller assembly 130 to reservoir 110, and to direct air into tube 174 and infused air out through opening 172. Cap base 170 may be securely placed on reservoir 110 with the aid of gasket 112 on the neck 114 of reservoir 110. Cap base 170 may be part of controller assembly 130 or may be used as a cap for reservoir 110. In such embodiments, switching reservoirs is very simply accomplished by pulling controller assembly 130 off of base cap 170 and placing in on a different reservoir with another base cap installed.

Figure 5:
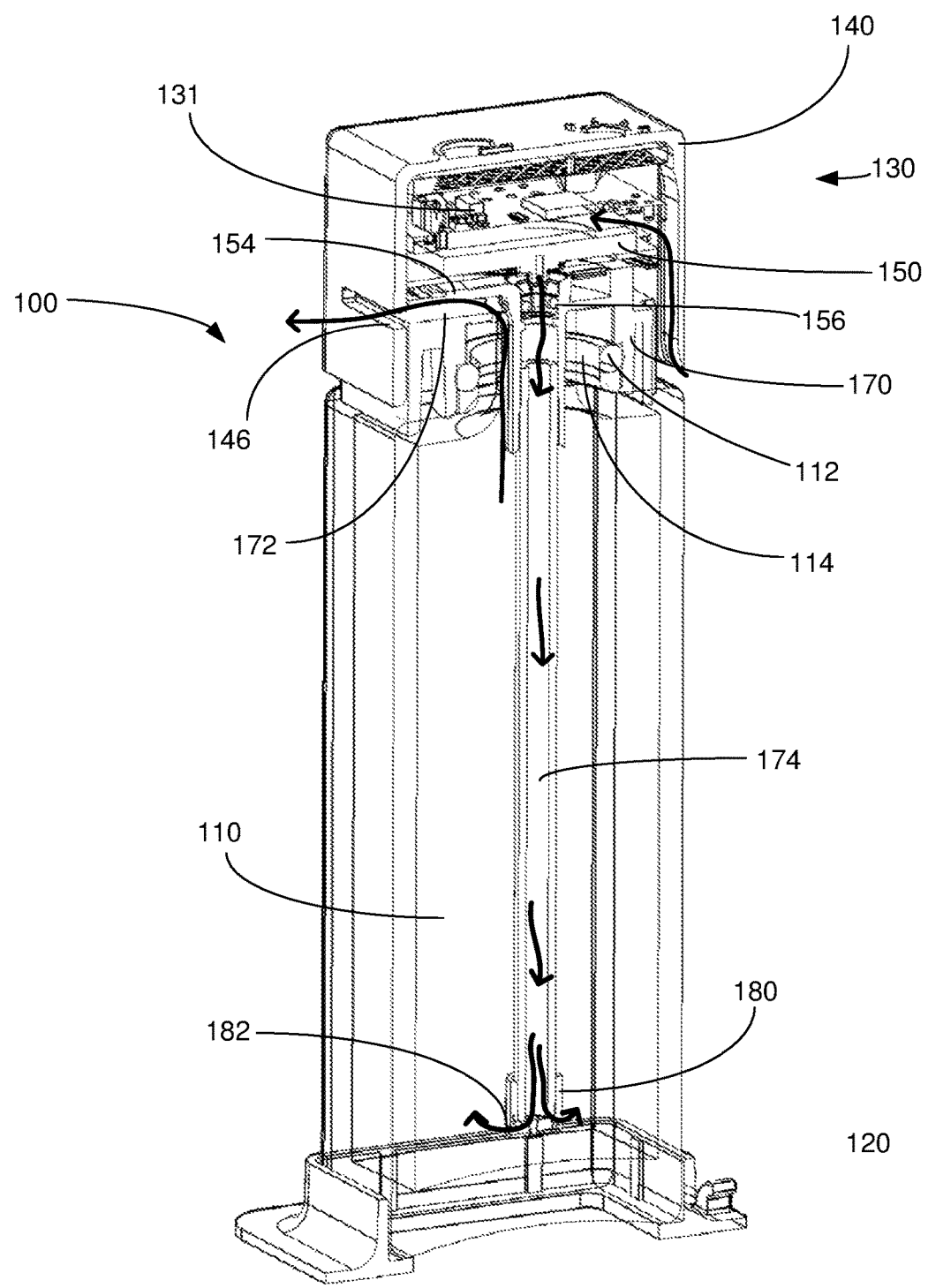
FIG. 5 shows a cross-sectional view of the diffuser and air pathway lines for the essential oils diffuser of FIG. 1.
Figure 6:
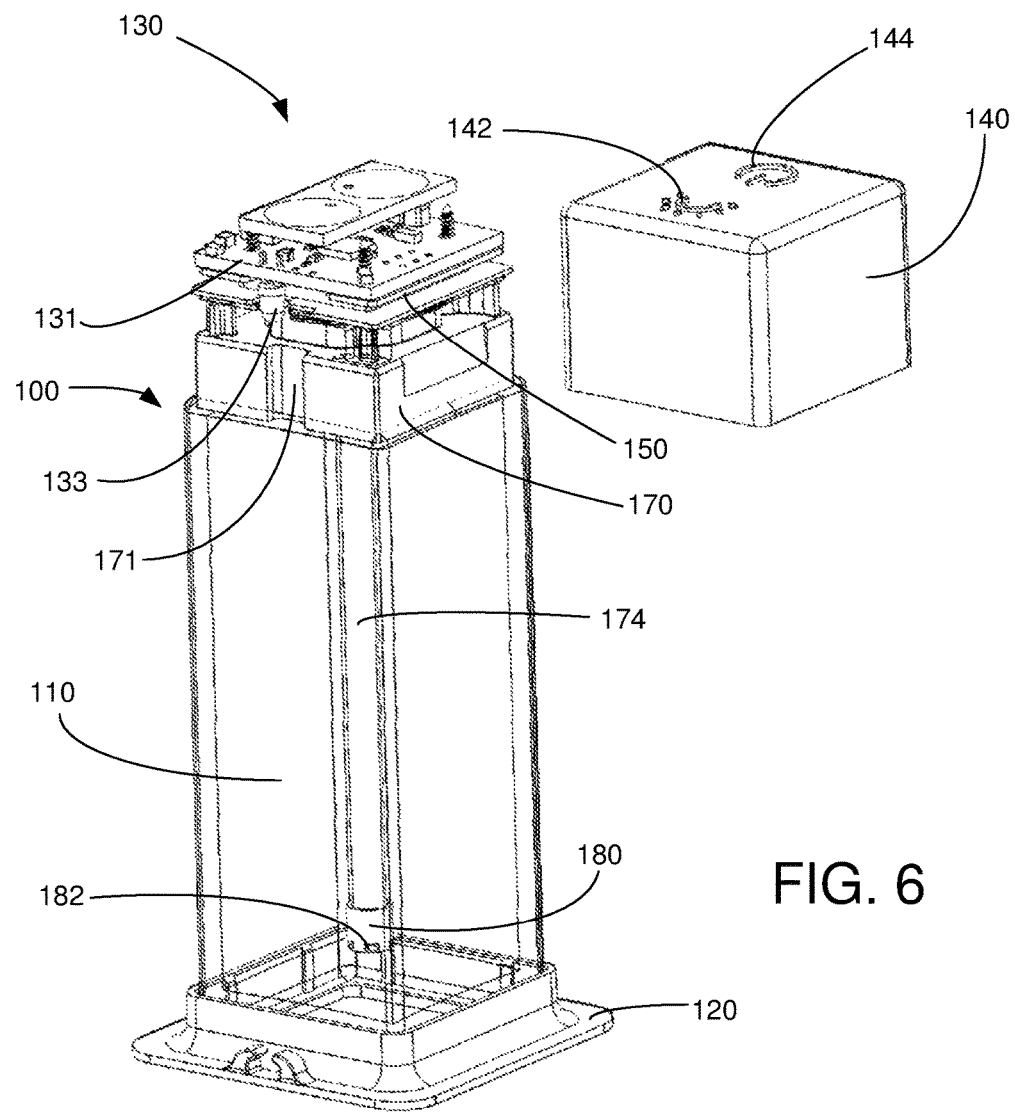
FIG. 6 shows a partially disassembly view with the cap of the controller assembly removed.

Turning now to FIGS. 5 and 6, the path of air through diffuser 100 can be easily seen. Fresh air enters under the rear of protective cap 140, along channel 171 in cap base 170, into air pump 150, and is then pumped down through cap base 170 and into tube 174 into reservoir 100. At the bottom of tube 174, bubbler 180 includes a plurality of openings 182 to create bubbles when air is pumped into essential oils in reservoir 110. The bubbles may then rise through the essential oils in reservoir 110, ideally bursting at the surface. The oil infused air can then exit though cap base 170 channel 172 and out through exhaust opening 146.

Bubbler 180 may be designed with different sizes and configurations of openings 182 depending on the size and frequency of bubbles desired, as well as depending on the viscosity of the essential oil to be diffused. For example, smaller openings 182 may provide small bubbles, which may the provide maximum efficiency in diffusing oils into the air within the bubbles as the available surface area per volume of air is maximized. In some embodiments, the sound of the bubbles can be tuned to generate an aesthetically pleasing sound based on the size and frequency of the bubbles based, again, on the number and sizes of openings 182 and the viscosity of the oil. For example, bubbler 180 may include 6 openings 182 with a diameter of less than 1 mm for smaller and faster bubbles, or 12 openings 182 with a diameter of greater than 1 mm for slower and larger bubbles.

Reservoir 110 may consist of an easily removable glass or molded polymer body that is optimized dimensionally with the diffuser for greatest effect by allowing the most oils to be diffused in an effective manner before requiring a refill. In some embodiments, the reservoir may be bottles that are provided with essential oils by distributors and manufacturers. It may also be fitted with specially designed cap base 170 as discussed above.

In some embodiments, exhaust ports or emitters can be a small series of holes or other physical opening in the cap 140 and cap base 170 or at a body at the top of the reservoir that allows the pressurized air and volatiles to escape into the space or room to be diffused. These holes or opening can be closed or regulated via a valve or mechanism, or by simply tightening the reservoir to the cap for long-term storage during periods of non-use. This design may have the advantage of very good diffusion rates (consumption of essential oil) that can create a noticeable and potent aroma from a very small package and low relative energy consumption. This may be a desirable feature for essential oil companies as it promotes consumption of the products.

Exemplary essential oils diffusers as described herein provide superior diffusion compared to a simple fan that can only evaporate or blow air onto the surface of the essential oil or saturated pad. In contrast, the micro air pump injects pressurized air into the bottom of the reservoir, delivering a long, uninterrupted performance with intense, crisp, and refreshing aromatic effect. Interestingly, a separate external or additional piezo micro air pump can be utilized that blows fresh air into the diffused air stream after it exits the diffuser to further distribute the aroma if desired.

In some embodiments, the micro air pump may be located within a very short distance of the point of diffusion, or air discharge. This would enable the internal warmth of the device due to its operation to be quickly carried with the pressurized air to the diffusion point, further enhancing diffusion efficiency. The illustrated designs and others may permit incoming air flow to flow past and cool all electronic components to increase the warmth of the input pressurized air introduced into the essential oil reservoir. However, if the design requires, it can be located further away for more design freedom.

In some embodiments, the micro air pump can be modulated to create different flow rates by varying the amplitude of the sinusoidal drive signal for adjustable flow. Or it can be controlled in an adjustable interval On/Off mode for periodic diffusion. Alternatively, the flow rate can be controlled by reducing the diffuser emmiter (exit) opening by adjusting a mechanism or tightening the reservoir bottle. Because of its small size, the micro air pump can be located unobtrusively and almost invisibly in many areas of the diffuser. One optional micro air pump may be only a few millimeters thick and have a footprint of only 20 mm×20 mm square. This permits the diffuser to achieve many novel, different, and even minimal designs that will create a differentiated look. Additionally, the LED can be modulated to create a different mood or lighting effect. The LED(s) may be positioned in the controller assembly 130 to provide a pleasing down-lit effect as seen in the glass essential oil well. A pleasing bubble action with constantly changing bubble patterns may be highlighted by the LEDs In other embodiments, the controller assembly 130 may also include wireless communication capability to allow for control from a wireless device such as a cell phone or other computer. Similarly, the control functionality may be modified in numerous ways with air flow and lighting modifications as desired.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, examples are meant to be illustrative only and should not be construed to be limiting in any manner.

The invention claimed is:

1. A device for diffusing essential oils into the air, the device comprising:
   a reservoir;
   a micro air pump assembly having an air intake and a pressurized air outlet; and
   a cap removably attachable to the reservoir body, wherein the cap includes:
   a tube in fluid connection between the outlet of the micro air pump and extending into the reservoir, the tube providing a path for pressurized air from the micro air pump assembly into the reservoir below an oil level in the reservoir body;
   an outlet for the air with infused essential oils to disperse into the air around the device and away from the air intake of the micro air pump assembly; and
   a controller for controlling the micro air pump and operation of the device.

2. The device of claim 1, further comprising at least one LED.

3. The device of claim 1, wherein the micro air pump assembly generates at least 500 Pa of pressure.

4. The device of claim 1, wherein the micro air pump consumes less than 2 Watts when operating.

5. The device of claim 1, wherein the micro air pump assembly further includes a bubbler connected to the end of the tube below the oil level in the reservoir body.

6. The device of claim 5, wherein the bubbler includes a plurality of openings.

7. The device of claim 1, wherein the micro air pump is a piezo air pump.

8. A device for infusing air with essential oils, the device comprising:
   an essential oils reservoir;
   a micro air pump;
   a tube extending from the output of the micro air pump to below the surface of the essential oil in the essential oils reservoir and proximate to the bottom of the reservoir; and
   a bubbler attached to the end of the tube proximate to the bottom of the reservoir; and
   a controller for controlling the micro air pump and operation of the device.

9. The device of claim 8, further comprising at least one LED.

10. The device of claim 8, wherein the micro air pump assembly generates at least 500 Pa of pressure.

11. The device of claim 8, wherein the micro air pump consumes less than 2 Watts when operating.

12. The device of claim 8, wherein the micro air pump assembly further includes a bubbler connected to the end of the tube below the oil level in the reservoir body.

13. The device of claim 12, wherein the bubbler includes a plurality of openings.

14. The device of claim 8, wherein the micro air pump is a piezo air pump.

15. A method of infusing air with essential oils, the method comprising:
   providing an essential oils reservoir;
   providing a micro air pump;
   extending a tube from the output of the micro air pump to below the surface of the essential oil in the essential oils reservoir and proximate to the bottom of the reservoir; and
   directing air through the tube from the micro air pump thereby creating bubbles in the essential oils reservoir by controlling the micro air pump with a controller.

16. The method of claim 15 wherein the micro air pump consumes less than 2 Watts of power.

17. The method of claim 15 wherein the micro air pump provides at least 500 Pa of pressure.

18. The method of claim 15 wherein the micro air pump is a piezo air pump.

19. The method of claim 15 further comprising, providing a bubbler attached to the submerged end of the tube and having a plurality of holes such that air forced through the holes forms bubbles in the essential oils reservoir.

20. The method of claim 15 further comprising, causing the bubbles to burst and channeling the infused air within the bubbles away from the micro air pump.

* * * * *